US008097295B2

(12) United States Patent
Roper et al.

(10) Patent No.: US 8,097,295 B2
(45) Date of Patent: Jan. 17, 2012

(54) METHOD OF MAKING NANOPARTICLES BY ELECTROLESS PLATING

(75) Inventors: Donald Keith Roper, Salt Lake City, UT (US); Wonmi Ahn, Salt Lake City, UT (US); Benjamin Jeppson Taylor, West Jordan, UT (US); Analía G. Dall'Asén, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 516 days.

(21) Appl. No.: 12/038,088

(22) Filed: Feb. 27, 2008

(65) Prior Publication Data
US 2009/0213368 A1 Aug. 27, 2009

(51) Int. Cl.
*B05D 5/12* (2006.01)
(52) U.S. Cl. ............... 427/125; 427/123; 427/126.1; 427/126.5
(58) Field of Classification Search ............... None
See application file for complete search history.

(56) References Cited

OTHER PUBLICATIONS

Bhuvana and Kulkarni "Optimizing growth conditions for electroless deposition of Au films on Si(111) substrates", Bull. Mater. Sci., vol. 29, No. 5, Oct. 2006, pp. 505-511.*
Ker et al. "A Hybrid Segmentation Method for Nano-particle Characterization", Aug. 2006 http://www.iienet.org/uploadedfiles/IIE/Technical_Resources/Archives/319.pdf.*
Zhao, et at, "The Extinction Spectra of Silver Nanoparticte Arrays: Influence of Array Structure on Plasmon Resonance Wavelength and Width", J. Phys. Chem. B, 2003, vol. 107, pp. 7343-7350.*
Lin and Chen, Carrier Transfer Induced Photoluminescence Change in MetaPSemiconductor Core-Shell Nanostructures', AppI. Phys, Lett., 2006, vol. 88, pp. 161911-161913.*
Zeman and Schatz, "An Accurate Electromagnetic Theory Study of Surface Enhancement Factors for Ag, Au, Cu, Li, Na, AJ, Ga, in, Zn, and Cd", J. Phys. Chem. 1987, vol. 91, pp. 634-643.*
Spadavecchia, et al, "Au Nanoparticles Prepared by Physical Method on Si and Sapphire Substrates for Biosensor Applications", J. Phys. Chem. B., Sep. 2005, vol. 109, pp. 17347-17349.*
Roper "Determining surface plasmon resonance response factors for deposition onto three-dimensional surfaces", Chemical Engineering Science, 2007, v. 62, pp. 1988-1996.*
Becker, et al,, "The Adsorption of Gold to Galena Surfaces: Calculation of Adsorption/Reduction Energies, Reaction Mechanisms, XPS Spectra, and STM Images", *Geochimica et Cosmochimica Acta.*, 1997, vol. 61, pp. 3565-3585.
Roper, "Determinging Surface Plasmon Resonance Response Factors for Deposition Onto Three-Dimensional Surfaces", *Chem. Eng. Sci.*, 2007, vol. 62, pp. 1988-1996.

* cited by examiner

*Primary Examiner* — Yelena G Gakh
(74) *Attorney, Agent, or Firm* — Foley & Lardner LLP (57) ABSTRACT

A plurality of gold nanoparticles disposed on a surface of a substrate includes nanoparticles having an average particle density greater than $1.8 \times 10^{11}$ particles per squared centimeter of the surface. The gold nanoparticles include a monomodal diameter distribution and an average diameter capable of being arbitrarily controlled between about 5 nm to about 300 nm. The surface may be a three-dimensional surface or an internal surface.

2 Claims, 8 Drawing Sheets

METHOD OF MAKING NANOPARTICLES BY ELECTROLESS PLATING

STATEMENT REGARDING FEDERALLY-SPONSORED RESEARCH OR DEVELOPMENT

This invention was made with Government support under ECS0709456 and R03 EB004886 awarded by the National Science Foundation and National Institutes of Health. The Government may have certain rights in the invention.

BACKGROUND OF THE INVENTION

The present invention relates generally to the field of nanoparticles and more particularly to nanoparticles having tunable optical properties.

An article by Spadavecchia et al., entitled "Au Nanoparticles Prepared by Physical Method on Si and Sapphire Substrates for Biosensor Applications," *J. Phys. Chem. B*, 109 (37), 17347-17349, 2005, which is incorporated herein by reference in its entirety, describes the preparation of gold (Au) nanoparticles formed by thermal evaporation of a thin Au film and subsequent annealing. The Au nanoparticles were reported to have an average diameter of 15.8 nm and a particle density of $1.8 \times 10^{11}$ $cm^{-2}$.

SUMMARY OF THE INVENTION

One embodiment of the invention relates to a method of making nanoparticles, including providing a substrate comprising a tin-sensitized surface, forming an island film by reduction of metal ions onto the tin-sensitized surface, and annealing the island film to form the nanoparticles.

Another embodiment of the invention relates to a method of making nanoparticles, including performing electroless plating in a solution comprising a nanoparticle precursor to form an island film on a surface, and annealing the island film to form the nanoparticles, wherein an average diameter of the nanoparticles is capable of being arbitrarily controlled during processing from about 5 nm to about 300 nm.

Another embodiment of the invention relates to a plurality of gold nanoparticles disposed on a surface of a substrate, wherein the nanoparticles have an average particle density greater than $1.8 \times 10^{11}$ particles per squared centimeter of the surface.

BRIEF DESCRIPTION OF THE DRAWINGS

FIGS. 6A-C are SEM images of the same Au structures on a quartz slide.

DETAILED DESCRIPTION OF THE EMBODIMENTS

Introduction/General

Optically tunable nanostructures are provided for applications including electronics, micro-electromechanical systems (MEMS) devices, diagnostics, biosensing, spectroscopy and microscopy. In particular, an advantage of the embodiments is a method of making both island films and nanoparticle films having tunable size, shape, surface density, and morphology giving rise to tunable optical properties. Order-of-magnitude enhancement of spectroscopic (e.g., Raman, UV-vis) signal is achieved via predictably adjustable resonant surface plasmon frequency.

Molecular metal molecules deposited by electroless (EL) plating onto surfaces are thermally transformed into continuous island films and/or isolated nanoparticle films that enhance spectroscopic signal from adjacent dielectric(s) and analyte(s) via resonant surface plasmons. The enhancement may be optimized predictably by adjusting maximum resonant plasmon frequency via changing physical composition and dimensions of film and its constituent entities as well as distance between adjacent entities and matrix regularity. Adjustable variables to affect these changes include state (e.g., temperature, pressure, composition) and application (e.g., time, velocity, evaporation rate, droplet size) of electroless solutions as well as state (e.g., temperature, pressure) and application (e.g., time, associated velocity) of thermal transformation. Modulating deposition rate by changing Au(I) content in electroless (EL) plating solution or by using droplets, and adjusting annealing conditions offer methods of controlling size, morphology, orientation and optical properties of EL island films and nanoparticles.

Additional advantages of the embodiments include an inexpensive, rapid, scale-able, and safe molecule-by-molecule 'bottom-up' fabrication approach. Island films or nanoparticle films may be formed on multifaceted or curved surfaces, such as 3D or internal surfaces, at ambient conditions without requiring conductive substrates or expensive, sophisticated equipment. Furthermore, EL plating is compatible with continuous manufacturing using, for example, microfluidics, roll-to-roll, inkjet, screen printing, or aerosol deposition techniques.

By controlling the island film thickness and/or annealing conditions, the average diameter of the nanoparticles is capable of being arbitrarily controlled to any diameter from about 5 nm to about 300 nm, such as from about 10 nm to about 150 nm. The average particle density of the nanoparticles is greater than $1.8\times10^{11}$ particles per squared centimeter of the surface, such as about $2.0\times10^{11}$ to $2.8\times10^{11}$ particles per squared centimeter of the surface, for example about $2.3\times10^{11}$ to $2.6\times10^{11}$ particles per squared centimeter of the surface.

Materials

Solutions were made using distilled, de-ionized water that was degassed (DDD-$H_2O$) to mitigate undesired oxidation. $HAuCl_4.3H_2O$ (99.9+%), $AgNO_3$ (99.0+%), anhydrous $SnCl_2$ (99.9+%), trifluoroacetic acid (99.0%), and NaCl were obtained from Sigma-Aldrich (St. Louis, Mo.) and used as received. $Ba(OH)_2.8H_2O$ (98.9%), $Na_2SO_3$ (98.6%), $HNO_3$, NaOH, and formaldehyde were obtained from Mallinckrodt (Phillipsburg, N.J.). Ammonium hydroxide (EMD Chemicals Inc., Darmstadt, Germany) was handled in a chemical fume hood using gloves, lab coat and safety glasses to prevent corrosion and/or burns.

Fused quartz slides (GE 124 fused quartz, Chemglass Inc., Vineland, N.J.) were immersed in a 25% $HNO_3$ for 30 minutes to improve Au adhesion on the surface. After etching, the slides were rinsed throughoutly with DDD-$H_2O$ and dried with $N_2$ gas. The slides plated for 30 and 60 minutes were HF etched for 20 minutes before $HNO_3$ etching and were not washed with DDD-$H_2O$ after Au plating, as described in the text. Other substrates may include quartz, glass, mica, silicon, or combinations thereof.

Sodium gold sulfite solution may be synthesized according to the method described in U.S. Pat. No. 6,126,807 to Abys et al., which is incorporated herein by reference in its entirety. 0.1 g of $HAuCl_4.3H_2O$ was dissolved in 0.5 mL aqua regia ($HNO_3$:HCl=3:1) and boiled to 84° C. to evaporate $HNO_3$ while stirring 0.03 g of NaCl was added and boiled to 94° C. until dry to produce $Na(AuCl_4)$. $Na(AuCl_4)$ was then dissolved in 1.8 mL of DDD-$H_2O$ and heated to 80° C. Under stirring, 0.1 g of $Ba(OH)_2.8H_2O$ was added and yellow solution changed its color to dark amber. After complete dissolution, a concentrated aqueous NaOH solution that was produced by dissolving 0.06 g of NaOH in 120 μL of DDD-$H_2O$ was added to form a greenish brown precipitate. The solution was boiled to dryness and slurried in 1.8 mL of cold DDD-$H_2O$, followed by filtration using a fine filter paper and washing with cold DDD-$H_2O$. Then, the precipitate was slurried in 1.8 mL of cold DDD-$H_2O$, heated to 50° C. with stirring, cooled, filtered, and washed with cold DDD-$H_2O$, and the precipitate was collected. This slurry/wash was repeated three times. The final washed precipitate was slurried again in 2.3 mL of DDD-$H_2O$ and heated to 60-65° C. While stirring, 0.36 g of $Na_2SO_3$ was dissolved under $N_2$ gas feed. During ~45 minutes of stirring at 60-65° C. under $N_2$ gas feed, the color of the precipitate changed to purple or blue. Finally, the precipitate was filtered through the fine filter, washed with a little hot DDD-H$_2$O, and the filtrate (sodium gold sulfite solution; Na$_3$[Au(SO$_3$)$_2$]) was stored under a nitrogen overlayer in a brown vial at 4° C.

Surface Preparation

A tin-sensitized surface is formed by adsorbing tin ions onto a surface. For example, a tin-sensitized surface was formed on a silicon dioxide surface via the reaction: SnCl$_2$→Sn$^{2+}$+2Cl$^-$. Surfaces, sensitizers, and sensitization/activation methods can be those described in U.S. Pat. No. 4,042,730 to Cohen, et al. and in McDermott, J. *Plating of Plastics with Metals*; Noyes Data Corp., Park Ridge: N.J., 1974 especially chapter 1 and pp 180-182; all of which are incorporated herein by reference in their entirety. For example, the surface can be a polymeric surface. Quartz slides were sensitized by immersion in a solution of 0.026 M SnCl$_2$ and 0.07 M trifluoroacetic acid for 3 minutes, followed by rinsing in a warm DDD-H$_2$O (50-55° C.) and drying with N$_2$ gas. Preferably, the Sn$^{2+}$ 'sensitizer' is covalently adsorbed onto the SiOH surface. Stannous ions (Sn$^{2+}$) sensitize the surface for subsequent chemistries, such as for adsorption of catalytic nuclei.

The tin-sensitized surface is activated by depositing a layer of noble metal on the surface. The noble metal may be gold, silver, tantalum, platinum, palladium or rhodium. For example, the noble metal is silver and is formed by reducing silver ions onto the tin-sensitized surface. The silver layer may comprise a silver-silver oxide thin film, island film, or nanoparticles formed by the reduction of silver ions (Ag$^+$) onto a Sn$^{2+}$ sensitized surface via the reaction: 2 Ag$^+$+ Sn$^{2+}$→2Ag+Sn$^{4+}$. Although it is believed that the tin ions remain bonded to the surface after formation of the noble metal layer, it shall be understood that a tin-sensitized surface need not require the presence of tin after the noble metal layer is formed. In one embodiment, 0.029 M ammoniacal AgNO$_3$ was prepared to activate the Sn$^{2+}$ sensitized surface. For example, the ammoniacal silver nitrate solution may be prepared according to Sigma-Aldrich (procedure # HT 102) (2005), which is incorporated herein by reference in its entirety. 1.0 mL of 10% AgNO$_3$ was titrated with concentrated ammonium hydroxide drop by drop while stirring in a hood until the precipitate was completely dissolved. 3.33 mL of 3% NaOH was added and ammonium hydroxide titration was performed again until the precipitate just dissolved. Solution was diluted and filtered using a fine filter paper. After 2 minutes in Ag solution, quartz slides were rinsed with warm DDD-H$_2$O and dried with N$_2$, resulting in isolated particles of silver-silver oxide material, which adhere strongly to the surface. The silver layer, which may comprise an island film or clustered nanoparticles, may then either be (a) annealed to form silver nanoparticles, which may then, optionally, be galvanically displaced with a more noble metal to form nanoparticles of the more noble metal; or (b) galvanically displaced with a more noble metal to form nanostructures of the more noble metal, which may then, optionally, be annealed to form nanoparticles of the more noble metal.

Electroless Plating

Electroless (EL) plating of nanoparticle precursors is performed by galvanically displacing the layer of noble metal with the nanoparticle precursor. Preferably, the noble metal layer is less noble than the nanoparticle precursor. The nobility of metals may be determined by the galvanic series. For example, depending on the environment, the galvanic series may be: Pd>Pt>Au>Ag>Ti>Mo>W>Ta>Cr>Ni>Sn.

In one embodiment, the layer of noble metal is silver and the EL plating is performed in a solution containing of dissolved Na$_3$Au(SO$_3$)$_2$ to form a gold island film. For example, a solution containing metal ions, such as gold ions (Au$^{1+}$), galvanically displaces Ag to form an elemental Au surface via the reaction: Au(SO$_3$)$_2$$^{3-}$+Ag→Au+Ag$^+$. Although it is believed that the tin ions of the tin-sensitized surface remain bonded to the surface after galvanic displacement of Ag with Au, it shall be understood that a tin-sensitized surface bonded to an EL island film need not require the presence of tin after EL plating is performed. For example, EL plating of Au on a tin-sensitized silicon dioxide surface may, but need not, form Au—Si bonds or Au—Sn bonds. Without wishing to be bound to any particular theory, it is believed that Au nanoparticles are formed upon thermal annealing by mobile Au atoms that are located farther away from the tin-sensitized Si surface, while the Au atoms nearest the tin-sensitized Si surface remain immobile. This EL chemistry avoids hazardous reagents, such as concentrated hydrofluoric acid used to plate Au(III) from potassium tetrachloroaurate, and minimizes the use of Ag compared with galvanic substitution of vacuum evaporated Ag island film with gold. EL deposition avoids formation of a SiO$_2$ layer on the Au film surface via out-diffusion of Si that occurs during vapor deposition. Stabilization of Au reduction by formation of Au—Au metal bonds in dimers and islands has been confirmed by an ab initio cluster approach performed by Becker, U.; Hochella, M. F., Jr.; Vaughan, D. J., *Geochim. Cosmochim. Acta* (1997) 61, 3565-3585, which is incorporated herein by reference in its entirety.

The thickness of the island film can be varied from about 1 nm to about 100 nm, preferably less than 50 nm, such as about 2 nm to about 35 nm, for example about 5 nm to about 25 nm, by adjusting the solution deposition time and/or method. For example, EL plating is performed by substantially immersing the surface in the plating solution. Ag derivatized quartz slides were immersed in a Au plating solution (Na$_3$Au(SO$_3$)$_2$: solution of 0.127 M Na$_2$SO$_3$ and 0.625 M formaldehyde=1: 10) for the duration of desired deposition times. The deposition time can be varied from about 1 sec to greater than about 1 hr, such as from about 5 sec to about 10 min, preferably from about 10 sec to about 1 min. Au plated slides were then thoroughly rinsed with 25° C. DDD-H$_2$O and dried with N$_2$ gas.

Alternatively, EL plating is performed by depositing discrete droplets of plating solution onto the surface. For example, the droplet has a volume less than about 20 µL, preferably less than about 10 µL, such as about 1 to about 5 µL. After the quartz slide was etched in HNO$_3$, and Sn and Ag was deposited, a drop of 1 to 5 µL gold sulfide solution was placed on the slide. A polypropylene container allowed the drop to remain in a N$_2$ environment during the deposition period. Afterwards, the Au drop-plated slide was DDD-H$_2$O washed and N$_2$ gas dried.

Other methods of depositing droplets of solution can also be used. For example, the solution droplets can be deposited using microfluidics, roll-to-roll processing, inkjet, aerosol, spray coating, screen printing or other deposition techniques. The evaporation rate of the droplet can also be varied by changing the droplet volume, deposition atmosphere and pressure.

Thermal Treatment

The physical and optical properties of the deposited island films and/or nanoparticles can be tuned by varying the thermal treatments. For example, the temperature and time of the thermal treatment can be varied from minutes to hours at 200° C. to 900° C. A low-temperature anneal can initially be performed at about 200° C. to about 400° C. for about 1 hr to about 5 hr. Optionally, a high-temperature anneal can be subsequently performed at about 600° C. to about 900° C. for about 5 min to about 40 min.

After Au EL plating, quartz slides were immediately brought into a 250° C. furnace (Lindberg/Blue BF51732BC, New Columbia, Pa.) for 3-hour thermal annealing. At this temperature, the furnace had 13 minutes of ramp time for both heating and cooling, giving a ramp rate of ~17° C./min. This annealing process allowed deposited Au islands to re-arrange, resulting in a more uniform Au surface. For some of the Au plated slides, further annealing at 800° C. was performed for 20 minutes in a 9×9.5×13" furnace at a heating/cooling ramp rate of ~9° C./min. The furnace was purged with a continuous $N_2$ gas at 3.52 SLPM throughout the process.

Nanoparticles

The nanoparticles (NP) that are formed upon annealing can be tuned to have any arbitrary, predetermined diameter from about 5 nm to about 300 nm, such as from 10 nm to 150 nm, and more specifically from about 20 nm to about 90 nm. Ultra-small nanoparticles can have an average diameter of about 5 nm to 15 nm, such as about 9 nm to about 11 nm. The nanoparticles can have an average diameter in the optically-relevant size range of about 50 nm to about 70 nm, such as about 55 nm to 65 nm. The distribution of diameters is preferably a monomodal distribution. Preferably, at least 95% of the nanoparticles in a plurality have a diameter within about 20 nm, such as about 5 nm, of the average diameter of the plurality. The average particle density of the nanoparticles is greater than $1.8 \times 10^{11}$ particles per squared centimeter of the surface, such as about $2.0 \times 10^{11}$ to $2.8 \times 10^{11}$ particles per squared centimeter of the surface, for example about $2.3 \times 10^{11}$ to $2.6 \times 10^{11}$ particles per squared centimeter of the surface. The nanoparticle diameter and density is preferably measured using watershed analysis of a micrograph, such as a SEM or AFM micrograph, of a portion of the surface. Preferably, the micrograph used for watershed analysis is sufficient representative of the surface. For example, a confidence interval is preferably 95%. The size of the micrographed portion of the surface is preferably greater than about (500 nm×500 nm), such as about (1 µm×1 µm) to about (50 mm×50 mm). The number of nanoparticles in the micrographed portion of the surface is preferably greater than 50, such as about 20 to about 2,000.

Gold Sputtering

In order to compare morphological and optical quality of electroless plated Au films to the widely used simple method to produce thin Au film, the Au films were deposited by a Denton Discovery 18 sputter system (Moorestown, N.J.). Quartz slides were etched with 25% $HNO_3$ for 30 minutes to maintain the same initial slide conditions as the ones for electroless plating. In some slides, Cr was pre-coated for 15 seconds followed by Au sputtering to increase adhesion.

Characterization

Transmission UV-vis spectroscopy were recorded (Perkin-Elmer Lambda 35, Wellesley, Mass.) in a 350-800 nm wavelength range. To isolate the Au-plated slide for analysis, a 4.5×4.7 cm black paper pierced by a 1.5 mm diameter hole was inserted between incident light and sample inside the spectrophotometer. Etched quartz slides that had not been Au plated were used to obtain reference spectra. Spectra were fit to Gaussian curves (Origin(Pro) 7.5, OriginLab Corporation, Northampton, Mass.) to calculate peak intensity and full width at half maximum (FWHM) using the parameter W~0.849×FWHM and the minimum extinction as a baseline offset, $y_o$.

Scanning electron microscopy (SEM) was performed using a Philips XL30 ESEM FEG (FEI, Hillsboro, Oreg.). SEM micrographs were obtained by backscattered electron detector mode operating using a 15 kV electron accelerating voltage. The low vacuum setting was used and the pressure was varied independently for each image based on charging and desired resolution over a range of 0.4-1.2 Torr. Acquisition preprocessing software automatically stretches to accommodate low- and high-intensity in an image. This makes comparing contrast in SEM images with different ranges of intensity susceptible to error.

Atomic Force Microscopy (AFM) was performed in an air atmosphere using an AFM (WITec alpha 300, Ulm, Germany) with a maximum scan range of 100 µm×100 µm×20 µm. The 256×256-pixel micrographs were captured for different scanning areas (from 1×1 µm² up to 50×50 µm²) at a scan rate of 1 line/s. AFM contact and tapping modes were employed using highly-doped single crystal silicon tips with aluminum reflex coating (spring constant=3 µm; resonant frequency=60 kHz). Etched quartz slides that had not been Au plated were used to obtain reference images. Sample average roughness and cross-section curves in the AFM images were obtained with the WITec software, as described in WITec Project User Manual 2007, Chapter 7, p 66, which is incorporated herein by reference in its entirety.

Energy dispersive X-ray spectroscopy spectrum (EDS) was performed using an EDAX (HIT S3000N, Mahwah, N.J.) to show the proportion of the material constituents on the prepared surface.

X-Ray diffraction patterns was obtained from Philips X'Pert XRD (Almelo, Netherlands) to study crystalline structure of the sample with a fixed anode Cu source. X-ray was generated at 40 mA and 45 kV, and scanning position ranged from 20° to 99° (2θ). Collected data were analyzed using X-ray analysis software of PANalytical Inc. (Almelo, Netherlands).

Image Processing and Analysis of distributions and surface densities of Au islands, nanoparticles and voids in SEM and AFM micrographs of Au-coated quartz slides were characterized using image processing tools (Image Processing Toolbox 6.0) in MATLAB (v.7.4; MathWorks, Mass.). The open source computer program GIMP (v. 2.2.11; www.gimp.org) was used to manually mark particles that were missed by the watershed algorithm and unmark sodium crystals that were selected as nanoparticles. The 95% confidence intervals reported for all particle sizes was produced using Calc from the OpenOffice package (Version 2.3.1). The standard deviation and particle count were input into the confidence function to produce the confidence intervals reported herein.

Raman spectra of the samples were acquired in a backscattering geometry by means of a confocal Raman microscope (WITec alpha 300, Ulm, Germany) equipped with a single spectrometer and a thermoelectrically cooled CCD detector. Measurements were taken using 488-nm $Ar^+$ ion and 532-nm doubled Nd:YAG lasers ($\lambda_{exc}$) with a power ($P_{exc}$) of 15 mW. Light was focused onto the sample surface with a 10× objective (NA=0.25) for all the measurements. This objective produced a ~40-µm-diameter spot at the focal point. The same objective was used to collect the scattered light. Raman data was taken with different integration times (from 0.5 up to 5 s) and accumulations (from 10 up to 20) depending on the specific sample. The spectra were obtained as an average of three different measured locations of the samples surface. The Raman bands were analyzed using standard Gaussian functions with subtracted backgrounds.

Calculations

The simplified semi-analytical coupled dipole approximation (CDA) described by Schatz, *J. Phys. Chem. B* 2003, 107, 7343-7350, which is incorporated herein by reference in its entirety, was used for the light scattering and absorption calculations. In addition, for single sphere polarizability, it was found that a shift in the polarizability as a function of particle size was obtained by the exact solution to the approximation described by Wiscombe, *Applied Optics*, May 1980, Vol. 19, No. 9, which is incorporated herein by reference in its entirety. The exact solution and all light scattering calculations were solved using the open source Octave (v.3.0; www.Octave.org) computing package. The computational bottle neck to calculating results from the semi-anlytical solution to CDA was calculating a sufficient S matrix size, which Schatz, *J. Phys. Chem. B* 2003, 107, 7343-7350, suggested to be 800. It was found that a 50×50 NP array is sufficient to converge evaluation of the retarded dipole sum that previously required 800×800 array and yielded lower accuracy (ZKS03). The coupled dipole approximation was the only assumption that was used.

EXAMPLE 1

Preparation of Au Island Films by Immersion-EL Plating Method

Figure 1:
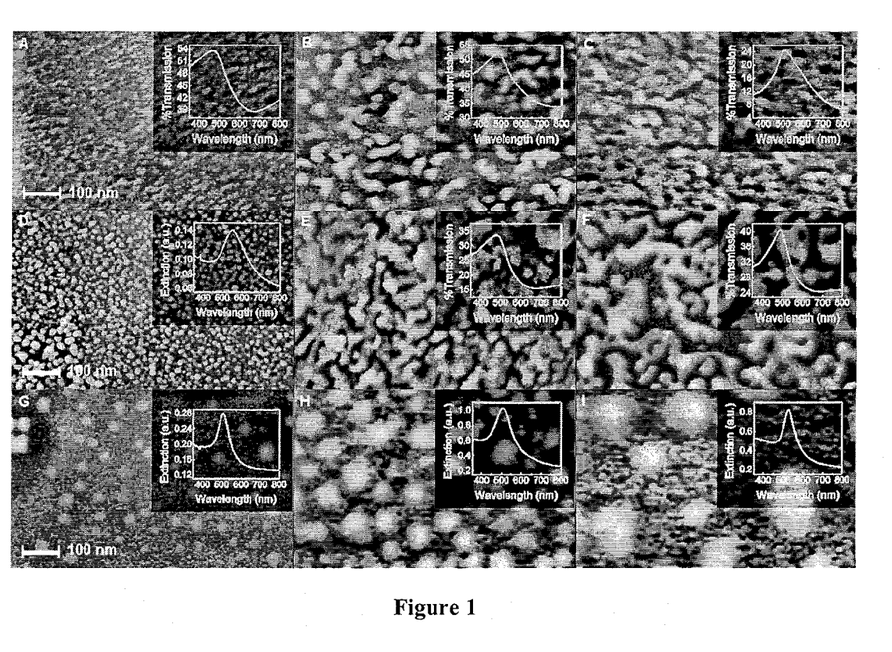
FIGS. 1A-C (top row of FIG. 1) show scanning electron microscopy (SEM) images of fused quartz slides after immersion in Au plating solution for (A) 0.33 min, (B) 1 mm, and (C) 4 min, respectively.
FIGS. 1D-F (middle row of FIG. 1) are SEM images of the slides in FIGS. 1A-C, respectively, after annealing for 3 h at 250° C.
FIGS. 1G-I (bottom row of FIG. 1) are SEM images of the slides in FIGS. 1D-F, respectively, after an additional high-temperature anneal for 20 min at 800° C. The insets in FIGS. 1A-I are transmission UV-vis spectra corresponding to each slide. Percent (%) transmission is shown in FIGS. 1A-C, 1E and 1F. Extinction in arbitrary units (a.u.) is shown in FIGS. 1D and 1G-I.

FIGS. 1A-C (top row of FIG. 1) shows SEM images of Au island films produced after immersing fused quartz slides in EL plating solution for (A) 0.33 (A), (B) 1, and (C) 4 minutes, respectively. The island films had a thickness of about (A) 3 nm (B) 8 nm, and (C) 32 nm. As can be seen in the SEM images, the Au island films do not completely cover the surface, and the underlying quartz surface is visible in the crevices between the islands. Because noble metals bind weakly to quartz surfaces, dissolved Au(I) reduces onto surface-associated Au(0) which has galvanically displaced Ag, producing an Au island film. Without wishing to be bound to any particular theory, it is believed that island film shapes are governed by underlying substrate composition (epitaxial) while their fractal dimension is determined by competition between terrace diffusion and edge diffusion of adatoms. Transmission UV-vis (T-UV) spectra inset in each image exhibit increased optical density (e.g., lower transmittance) and a maximum optical density at ~650 nm in FIG. 1A that upshifts in wavelength as film thickness increases. Without wishing to be bound to any particular theory, the optical density maxima is believed attributed to excitation of localized surface plasmon polaritons (SPP).

The EL-plated island films in FIGS. 1A-C were observed to photoluminesce. The T-UV spectra in FIGS. 1A-C show a feature appearing at ~500 nm wavelengths that increases in relative intensity and upshifts in wavelength as immersion time increases: (A) 467, (B) 481, and (C) 508 nm, respectively. Without wishing to be bound to any particular theory, this feature is attributed primarily to photoluminescence (PL) caused by electron transitions and recombination between filled d-bands and the Fermi-level conduction band in the gold (Au). Absorption of a photon at ~530 nm is sufficient to promote an electron from the top d-band to the Fermi-level conduction band. PL recombination of a Fermi-level electron (i.e., a band 6 electron from an occupied sp conduction band) with the d-band (i.e., band 5) hole then follows. The shape and bandgap energy of noble metal PL are predicted by the theory describing these transitions which occur at a quantum efficiency of $\sim 10^{-10}$. PL at ~500 nm increases with thickness in 2.5-nm and 5-nm thick Au island films but decreases with increasing thickness in films >60 nm. In FIGS. 1A-C the PL peak height increases with plating time and film thickness, as would an island film. It is believed, without wishing to be bound to any particular theory, that a second source for the ~500-nm feature is 'red photoluminescence' that has been observed upon excitation of Au thin films at 488.0, 514.5 and 832.8 nm due to collective optical absorption by resonant surface plasmon coupling inside cavities and between surfaces on both sides of island structures. This plasmon absorption decays radiatively, producing a broad spectral emission (550-750 nm) in thin films. The spectra in FIGS. 1A-C would exhibit red PL at excitation, but not emission, wavelengths since a 1-nm bandwidth light source and a broadband detector were used. SPP interactions due to red PL are excited more strongly in thinner (≦10 nm) Au films rather than thicker films. This trend is observed in FIGS. 1A-C as red PL intensity upon excitation at 488-nm decreases with increasing immersion time and film thickness. PL peaks in T-UV spectra from sputtered films do not exhibit red PL contributions to the same degree at 488 nm (see FIG. 2). Red PL is not produced by nanoparticles on Si surfaces but appears when spheroid shapes coalesce due to EL plating.

EXAMPLE 2

Preparation of Au Thin Films by Sputtering

Figure 2:
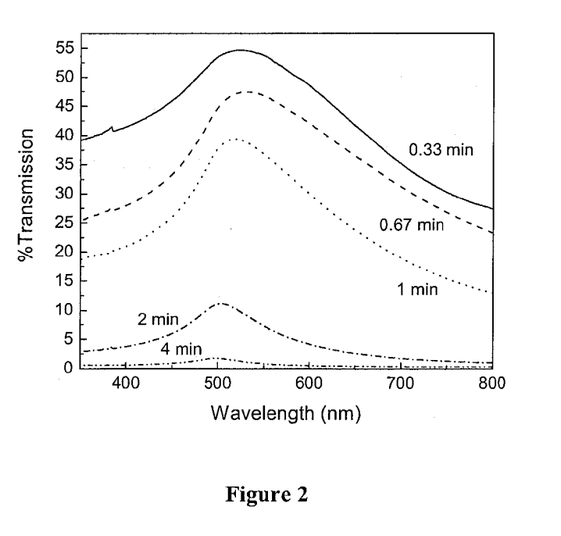
FIG. 2 shows transmission UV-vis spectra showing % transmission of Au sputtered quartz slides after sputtering at 20 nm/min for 0.33 min (solid line), 0.67 min (dash), 1 min (dot), 2 min (dash dot), and 4 min (dash dot dot).

For comparison with EL deposited films performed in Example 1, FIG. 2 shows T-UV spectra of Au thin films created by sputtering at a rate of 20 nm/min for times ranging from 0.33 min to 4 min. Values of extinction at 350 nm in sputtered film spectra increase in proportion to sputtering time up to ~2 min. Extinction profiles are calculated from % transmission profiles shown in FIG. 2 using the relation E=2−log(% T). Au deposits at an average rate of 40-50 nm/h in EL plating at conditions used in Example 1. But EL deposition rates are nonlinear, due to acceleration of Au reduction at pre-existing molecule-scale Au surfaces followed by deceleration of deposition as plating proceeds because surface free energy decreases as the dimensions of deposited Au increase. An EL deposition rate of ~8 nm/min during the first 4 min is estimated by comparing extinction values at 350 nm for EL plating with those for sputtering in Example 2.

Ultrathin (<10 nm) EL plated island films are smoother compared to sputtered films. Rough surfaces enhance scattering and broaden the PL feature, especially at energies lower (e.g. longer wavelengths) than the interband adsorption edge due to roughness quenching. This is due to electron-phonon and hole-phonon scattering processes after photon absorption and electron promotion that contribute to energy loss. For example, in FIG. 2, transmission PL maxima of sputtered films shift to lower energies as sputtering time decreases, and roughness increases. Rough, sputtered 20-nm Au films have been shown by Lin, H. Y.; Chen, Y. F., *Appl. Phys. Lett.* 2006, 88, 101914/1-101914/3, which is incorporated herein by reference in its entirety, to exhibit 5-fold higher PL intensity at ~500 nm than smooth evaporated 20-nm films.

Figure 3:
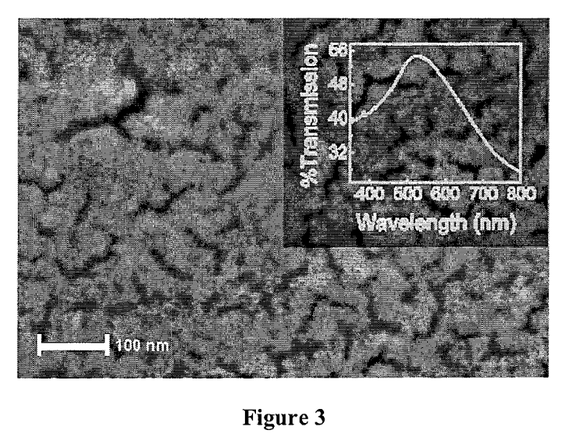
FIG. 3 shows a SEM image of a fused quartz slide after Au sputtering at a deposition rate of 20 nm/min for 0.33 min. Inset shows % transmission with peak height of 15.5% and full width half maximum (FWHM) of 155 nm.

To compare smoothness of EL films prepared in Example 1 to sputtered films prepared in Example 2, the following optical characteristics were considered: peak height (PH) and full width at half maximum (FWHM) of the PL feature at ~500 nm. One minute of EL film deposition (~8 nm thick) shown in FIG. 1B resulted in PH of 7% and FWHM of 92.9 nm. These values are much smaller than PH (15.5%) and FWHM (155 nm) of a slide sputtered for 0.33 min (6.6 nm thick) shown in FIG. 3. This difference occurs even though the contribution of red PL to the ~500-nm feature in FIG. 3 appears less than for the ultrathin EL film in FIG. 1B. This suggests that ultrathin (<10 nm) EL films in Example 1 are less rough than comparable sputtered films in Example 2.

Without wishing to be bound to a particular theory, this relative smoothness is attributed to a more uniform coating of the surface by $Sn^{2+}$. After 4 minutes of EL deposition in Example 1, the 32-n thick film in FIG. 1C exhibited PH of 13% and FWHM of 141 nm. These values are smaller than PH (20%) and FWHM (147 nm) of a slide sputtered for 1 min (20 nm thick) in Example 2, but larger than PH (8%) and FWHM (97 nm) of a slide sputtered for 2 min (40 nm thick), as shown in FIG. 2. This suggests that the difference in roughness between EL and sputtered thin films diminish as film thickness increases. That PH and FWHM increase with roughness is underscored by the trend in FIG. 2 that shows PL intensity sharpens and decreases in intensity as sputtering time increases to give a more uniform film in Example 2.

EXAMPLE 3

Preparation of Au NPs by Annealing at 250° C.

FIGS. 1D-F (middle row of FIG. 1) are SEM images of the Au island films prepared in FIGS. 1A-1C [immersion times: (A) 0.33 (A), (B) 1, and (C) 4 minutes in Example 1], respectively, after annealing for 3 h at 250° C. FIG. 1D shows that annealing the ultrathin EL island film in FIG. 1A at 250° C. (3 h) transformed it to nanoparticles (NPs) on the fused quartz surface. This yielded a localized surface plasmon resonant (LSPR) extinction band characteristic of Au NP at 552 nm (inset of FIG. 1D) with an intensity of 0.044 absorption units (AU) and FWHM of 95.4 nm. Watershed analysis of FIG. 1D yielded a mean particle diameter of 13.4±4.8 nm (95% confidence interval) and a particle density of $1.43 \times 10$ $cm^{-1}$. For comparison, a spectra of an aqueous suspension of 20-nm Au NP at 920 g Au $m^{-3}$ ($1.16 \times 10^{13}$ particles $cm^{-3}$) was examined in a 0.2-mm pathlength cell. The 20-nm NP suspension exhibited an LSPR band at 550 nm with an intensity of 0.14 AU and FWHM of 44.4 nm. NPs shown in FIG. 1D that had been annealed from the 3 nm EL film shown in FIG. 1A had a 1.6-fold lower physical density than equal-sized suspended particles and yielded an LSPR peak with a 2.1-fold larger FWHM and a 3.2-fold lower extinction.

The thin films in FIGS. 1B and 1C were annealed (250° C., 3 h) to produce images in FIGS. 1E and 1F, respectively. These thicker EL Au films in FIGS. 1B and 1C produced no visible Au NPs in body of the film upon annealing (250° C., 3 h), as shown by the persistence of island films in FIGS. 1E and 1F, respectively. These films required more extensive thermal treatments to produce NPs (see FIGS. 1H and 1I, respectively). Thermal annealing is believed to follow Stranski-Krastanov growth mode, improving bonding at interfaces between noble metal and semiconductor surfaces that typically exhibit poor mechanical and electrical bonding, depending on surface roughness, oxide content and cleanliness. High temperatures increase mobility of Au atoms on Si substrates as a function of vacuum, heating and cooling rates. Competing effects on optical density are produced by annealing. Optical density increases (i.e. transmissivity decreases) as annealing recrystallizes Au (111) surface atoms, increases Au grain size, reduces surface roughness and increases flat surface area up to 25-fold, thereby increasing optical reflectivity. For a 8-nm thick EL film, comparing images in FIG. 1B (unannealed) with 1E (annealed) illustrates this increased optical density. Annealing redistributed intense islands apparent in FIG. 1B more uniformly in FIG. 1E. But surface restructuring due to annealing also eliminates nanometer-scale features that resonate with incident photons orthogonal to the surface to produce SPP absorption, which reduces optical density. Annealing above 200° C. can also cause defects (cracks) by interdiffusion of Au and Si which reduces optical density.

For a 32-nm thick EL film, comparing images in FIGS. 1C (unannealed) and 1F (annealed) illustrates decreased optical density. Islands with more uniform surfaces that are separated by larger channels emerge in FIG. 1F. Because reduced surface roughness is common to these competing effects, T-UV spectra inset in both FIGS. 1E and 1F exhibit maxima in optical density that result from SPP interactions which are downshifted in wavelength after annealing to approach 650 nm. PL peak heights in FIG. 1B (7.2%) and C (13.3%) are reduced in FIGS. 1E (7%) and 1F (9.7%), respectively.

Morphological and optical transformations by thermal treatment were only observed in electroless Au plated slides. No change in the extinction spectrum after annealing and heating a chromium(Cr)-coated quartz slide sputtered with Au for 240 seconds was observed in films. Without wishing to be bound to any particular theory, it is believed that stronger adhesion between Au and Cr apparently reduces Au mobility on the Cr-coated slide relative to Au EL plated directly onto the quartz.

EXAMPLE 4

Preparation of Au NPs by Annealing at 800° C.

FIGS. 1G-I (bottom row of FIG. 1) are SEM images of the Au nanoparticles (FIG. 1D) and Au island films (FIGS. 1E-1D) after an additional high-temperature anneal for 20 min at 800° C. Corresponding inset extinction UV-vis (E-UV) spectra show maxima at 507, 506, and 526 nm, respectively. FIGS. 1G-I show that annealing for 20 min at 800° C. formed Au NPs in all three cases.

Figure 4:
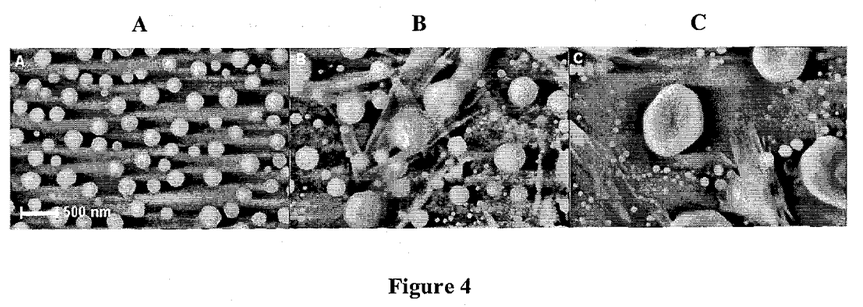
FIGS. 4A-C show SEM images of fused quartz slides that were immersed in Au plating solution for (A) 8 min, (B) 30 min, and (B) 60 min, respectively, after annealing at 250° C. for 3 h and an additional high-temperature anneal at 800° C. for 20 min. Weblike strands are NaCl-like crystal structures removed after rinsing with degassed (DDD)-$H_2O$.

FIGS. 4A-C show SEM micrographs of the Au NPs obtained after annealing at 250° C. for 3 hr and an additional high-temperature anneal at 800° C. for 20 min of fused quartz slides immersed for (A) 8, (B) 30, and (C) 60 min in EL plating solution, respectively.

Figure 5:
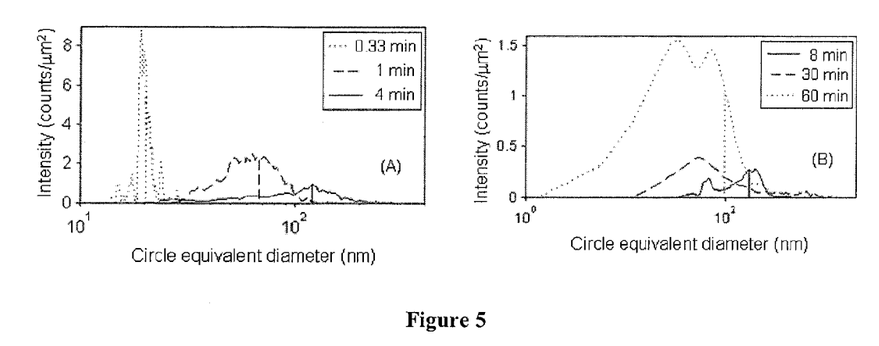
FIGS. 5A-B show distributions of measured circle-equivalent diameters obtained after annealing at 250° C. for 3 h and an additional high-temperature anneal at 800° C. for 20 min, after immersion in Au plating solution for (A) 0.33 min, 1 min, 4 min, and (B) 8 min, 30 min, 60 min.

FIG. 5A shows particle size distributions determined by watershed analysis from SEM images in FIGS. 1G-I (immersed for 0.33, 1 and 4 min, respectively). As immersion time increased from 0.33 to 1 to 4 minutes, average particle diameter increased from (20.30±0.39) to (67.6±1.1) to (120.0±4.2) nm, particle density in counts per $cm^2$ decreased from $3.5 \times 10^{10}$ to $9.0 \times 10^9$ to $2.5 \times 10^9$, and FWHM of the E-UV spectra increased from 8.52 to 40.30 to 67.85 nm, respectively. Peak intensity increases from 0.085 to 0.414 then decreases to 0.338. A three-fold increase in immersion time from 0.33 (FIG. 1G) to 1 min (FIG. 1H) produced nearly proportional increases in particle diameter (3.3-fold) and particle density (2.6-fold). Extinction peak intensity was enhanced 4.9-fold while FWHM increased 4.7-fold. The 22-nm NPs formed in FIG. 1G by annealing the 3-nm EL film in FIG. 1A had a 6.6-fold lower physical density than 20-nm suspended particles, but yielded an LSPR extinction peak with just 64% lower intensity and a 4.7-fold lower FWHM. The 67-nm NPs in FIG. 1H formed by annealing the 8-nm EL film in FIG. 1B had a 26-fold lower physical density but 2.4-fold higher extinction intensity than 20-nm suspended particles, due in part to increased scattering at larger NP dimensions. NPs with an average diameter of 67.6±1.1 nm were obtained by annealing ~8-nm Au films deposited by EL plating for 1 min (FIG. 1H). Particles with ~60 nm diameters have been reported by Zeman, E. J.; Schatz, G. C., *J. Phys.*

*Chem.* (1987) 91, 634-643, which is incorporated herein by reference in its entirety, to optimize surface enhancement in Raman spectroscopy.

FIG. 5B shows particle size distributions determined by watershed analysis from SEM images in FIGS. 4A-C (immersed for 8, 30 and 60 min, respectively). As immersion time increases from 8 to 30 to 60 minutes, average particle diameters produced by successive annealing changed from (169.0±2.5) to (266±22) to (97.0±9.5) nm, particle density changed from 7.2 to 4.3 to 12 counts per $cm^2 \times 10^{-8}$, and FWHM changed from 174 to 60.7 to 113 nm. Increasing deposition time enlarges Au nanoparticles (NP) and broadens the size distribution. The particle distribution and mean size for 60-minute EL deposition is skewed to smaller particle values by a large number of fine particles identified by watershed analysis.

Figure 6:
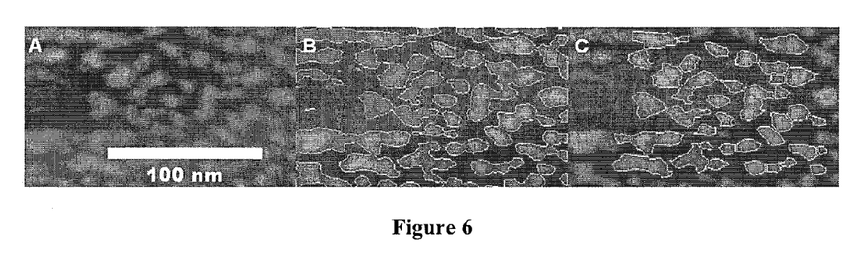
FIG. 6A is the original SEM image.
FIG. 6B shows the SEM image in FIG. 6A after the threshold method of segmentation is performed, resulting in particle 'fusion' with size distribution skewed by particles at the border.
FIG. 6C shows the SEM image in FIG. 6A after the watershed method is performed. Border removal quantitatively distinguishes particle size and number density.
Figure 7:
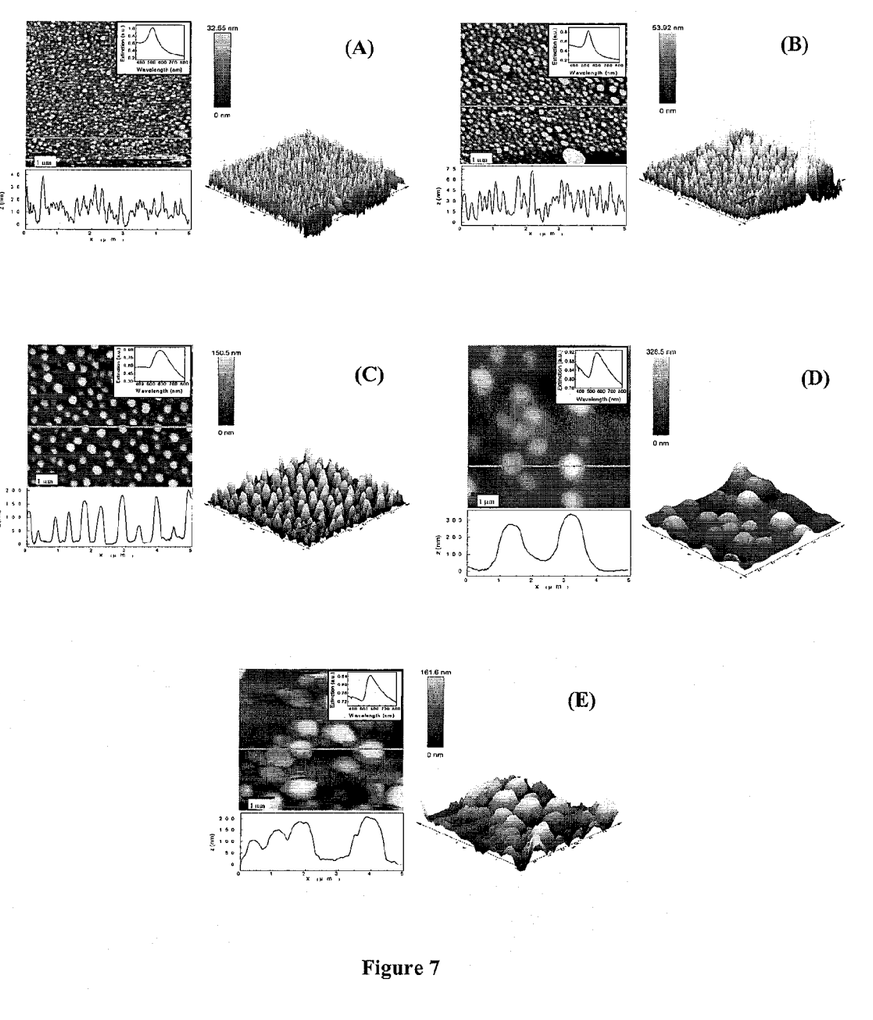
FIGS. 7A-E show atomic force microscope (AFM) images in 2D and 3D after quartz slides were immersed in Au plating solution for (A) 1 min, (B) 4 min, (C) 8 min, (D) 30 min, and (E) 60 min, respectively, and annealing at 250° C. and an additional high-temperature anneal at 800° C. AFM contact mode was employed for the images shown in FIGS. 7A, 7C, 7D and 7E. AFM tapping mode was used for the image shown in FIG. 7B. The scanning area is 5 μm×5 μm. The depth scale is indicated by the vertical bar. A representative cross-section is shown under each 2D image. The solid lines in the 2D images indicate the linear regions where the section analysis was performed. The insets in the 2D AFM images are extinction UV-vis spectra of each sample.

FIGS. 6A-C show that the watershed analysis method used herein achieves more accurate particle diameters and distributions than simple threshold methods which group particles into clusters. FIG. 6B shows that threshold algorithms can produce inaccurate particle size and shape measurements when adjacent particles are close and when poor image resolution and quality result in clumping.

To achieve the image analysis with boarder removal shown in FIG. 6C, a watershed transformation described by Meyer, F., *Sig. Proc.* (1994) 38, 113-125, which is incorporated herein by reference in its entirety, was adapted herein to segment the clumps and provide more accurate size and shape characterization. The watershed transform segments the image by relying on the image topology. The original image (FIG. 6A) is transformed into the complement, making local maxima into local minima and vice-versa. The watershed transform then begins to fill the local minima volume, hence the name. While filling if the local minima volume contacts an adjacent local minima volume a division is made and the particle becomes segmented. Two algorithms were developed to complement the adapted watershed transformation. The first algorithm stripped out particles that were touching the border of an image to exclude incomplete particles from measurements of particle size, shape and number density (FIG. 6C). Sodium crystal-like structures in FIGS. 4B and 4C, which disappeared when samples were rinsed copiously with DDD-$H_2O$ after EL deposition, were manually corrected after analysis by the watershed method to differentiate these structures from Au NPs. Crystals selected as particles were manually deselected and missed particles were manually reselected. The second algorithm was developed to select the appropriate gray scale to use when determining particle size and particle density from SEM images. Both these determinations rely on the user to define at what 'intensity' the particle ends and background noise begins. The algorithm used particle heights determined with a high degree of certainty using AFM, to define the appropriate distinction between particle intensity in SEM and background noise. In other words, the AFM images were used to calibrate the measurements of particle size and particle density in SEM images.

FIGS. 7A-E show 2D and 3D AFM images representative of samples obtained by immersion in EL plating solution for (A) 1, (B) 4, (C) 8, (D) 30, and (E) 60 min after annealing (250° C. for 3 h and 800° C. for 20 min). Insets in each image correspond to an extinction UV-vis spectra. AFM images in FIGS. 7A-B correspond to SEM images in FIGS. 1H-I, respectively, and AFM images in FIGS. 7C-E correspond to SEM images in FIGS. 4A-C, respectively. AFM contact mode was employed for the images showed in FIGS. 7A, 7C, 7D and 7E; while AFM tapping mode was used for the image showed in FIG. 7B. The scanning area is 5 μm×5 μm in all images. Representative line scans are shown at the bottom of each image, whose position is indicated by solid lines in the corresponding 2D image. In general, NP diameter increases and particle density decreases as EL plating time increases.

Table 1 shows particle diameters obtained by watershed analysis of SEM images and AFM images in the x-y plane at z=0. AFM diameters exceed SEM diameters in each case except for the 4-min deposition, due in part to convolution between probe tip and particle shape. The second algorithm (height analysis) was used to determine particle heights from the local minima of particle gradient obtained from inverted AFM images. Particle heights analyzed by height analysis (also called peak height method) in AFM are significantly lower than particle diameters estimated by watershed analysis of AFM images, due primarily to dome shapes appearing at larger immersion times, as well as a secondary contribution from tip-NP convolution.

TABLE 1

Particle diameters obtained from SEM and AFM images using the watershed method (WM) and the peak height method (PHM). The AFM (PHM) fits the SEM (WM) data better than the AFM (WM), which over predicts the particle size, due to tip convolution.

| Immersion time (min) | Particle SEM (WM) | diameter AFM (WM) | (nm) AFM (PHM) |
|---|---|---|---|
| 1 | 67.6 ± 1.1 | 111.9 ± 3.9 | 42.3 ± 1.1 |
| 4 | 119.6 ± 4.2 | 114.1 ± 4.4 | 49.48 ± 0.82 |
| 8 | 169.4 ± 2.5 | 241.3 ± 4.6 | 116.7 ± 2.6 |
| 30 | 266 ± 22 | 764 ± 80 | 183 ± 15 |
| 60 | 97 ± 13 | 580 ± 42 | 136.9 ± 8.7 |

Figure 8:
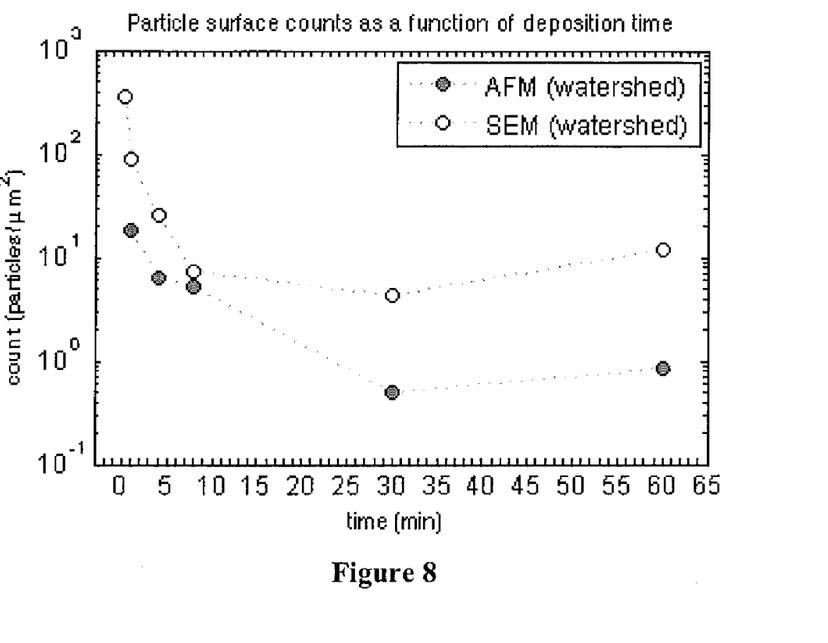
FIG. 8 shows plots of particle surface counts versus Au deposition time. Particle densities were estimated by watershed analysis of AFM (filled circles) and SEM (open circles) images for immersion times at 0.33 min, 1 min, 4 min, 8 min, 30 min and 60 min. The 0.33 min sample was damaged prior to AFM imaging and, therefore, a corresponding AFM data point is not shown for this sample.

FIG. 8 compares particle densities obtained by watershed analysis of AFM and SEM images. To find the particle densities on the Si surface, software counted the number of particles and divided by the total analyzed surface area. Compared with watershed analysis of SEM, AFM images return smaller particle counts per square micron by a factor of 5 at 1-minute immersion and by a factor of 14 at 60-minute immersion. Watershed analysis of SEM images appears to identify smaller ($\leq 5$ nm) particles more often than AFM images. Measured particle densities are most similar at 8 minutes, where SEM and AFM images each show monomodal distributions of 169-nm particles.

Figure 9:
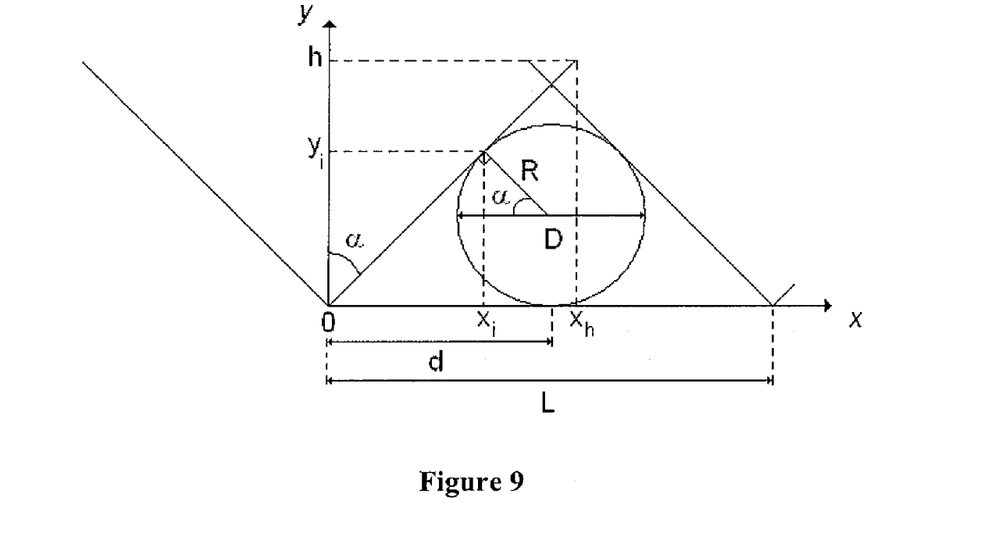
FIG. 9 shows a 2D schema of the geometry considered for the AFM measurements: triangle and circle shapes for the AFM tip and a nanoparticle on the sample surface, respectively.

Convolution between the conical AFM tip and Au surface profiles artificially increases Au dimensions in the x-y plane. NP sizes calculated in the x-y plane of AFM images are larger than those from corresponding SEM images for this reason. FIG. 9 shows a 2D schema of the AFM-NP geometries to estimate the effect of tip convolution on NP in the x-y plane as illustrated in. The AFM tip is approximated by a triangle of angle α~10° and height h, while the circular NP has diameter D and radius R. The tip apex located at the coordinate origin is a distance d from the base of the circle located at y=0. The distance d corresponds to an AFM-measured 'effective radius' and 2d=L, where L is the AFM-measured 'effective diameter'. Equations for tip and NP circle are:

$$y = \cot\left(\frac{\alpha}{2}\right)x \quad (1)$$

$$(x-d)^2 + (y-R)^2 = R^2 \quad (2)$$

Equations (1) and (2) yield a constant value for the theoretical ratio of 'effective' to actual particle dimension, $d/R = [1+\sin(\alpha)]/\cos(\alpha) = 1.19$. Table 2 shows d/R values measured for the respective AFM images analyzed in Table 1. The value of 2R corresponds to the maxima for each AFM-measured NP identified by watershed analysis or the peak height in an AFM scan line. The parameter 2d is the NP dimension measured by AFM in the x-y plane at z=0 or the peak base in an AFM scan line. Measured experimental values exceed the theoretical value of 1.19 in all cases. Correspondence is closest at 8 minutes immersion time (FIGS. 4A and 7C) where NPs approximate uniformly-sized spheres, and worst at 60 minutes (FIG. 1E) where NP geometries are irregular.

Sample roughness was found to correspond to particle size distribution. Table 2 also summarizes average roughness (AR) values, obtained from image topographies z(x,y), of each NP sample. These values are averages calculated from several images acquired in different regions of the respective samples. Comparing an AFM image with its corresponding AR shows that AR decreases as particle size distributions become more uniform. Samples immersed for 1 and 8 min (FIGS. 1A and 1C, respectively), which exhibit the most regular and uniform particle dimensions, have low AR values.

TABLE 2

Average roughness (AR) values in AFM image topography, z(x, y) and base-to-height ratios from AFM line scans.

| Immersion time (min) | AR (nm) | Measured d/R |
|---|---|---|
| 1 | 34.73 | 4.1 |
| 4 | 148.08 | 4.1 |
| 8 | 57.40 | 1.7 |
| 30 | 94.23 | 5.2 |
| 60 | 63.16 | 10.3 |

Figure 10:
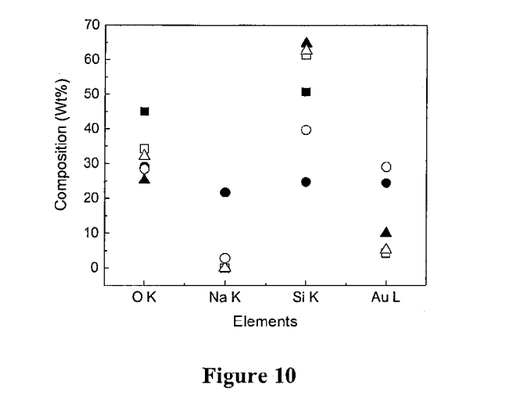
FIG. 10 shows a plot of measure energy dispersive X-ray spectroscopy (EDS) composition analysis in wt % for 6 different Au plated samples at various plating times and thermal treatment conditions: Au plated quartz slides for 8 min by Au droplet (filled squares) and by immersing in Au sulfite solution (open squares) after annealing at 250° C. for 3 h. Au plated quartz slides for 10 min by immersing in Au sulfite solution before thermal treatment (filled triangles) and after annealing at 250° C. for 3 h (open triangles). Au plated quartz slides for 30 min by immersing in Au sulfite solution after annealing at 250° C. for 3 h (filled circles) and after an additional high-temperature anneal at 800° C. for 20 min (open circles).

FIG. 10 shows weight percentages of four elements (O, Na, Si, and Au) in 6 different Au plated Si slides obtained by elemental analysis performed by EDS for samples prepared using different immersion times and thermal treatments. The letters K and L in abscissa of FIG. 10 refer to atomic shells. The 30-minute immersion times (open and filled circles) show relatively higher Au content and lower Si content than shorter immersion times. Samples washed with DDD-$H_2O$ after Au plating (open and filled squares and triangles) exhibited no sodium. The 30-minute data (open and filled circles) indicate sodium was reduced by annealing at 800° C. Oxygen in the data is believed to arises from quartz substrates ($SiO_2$) and oxygen in the air.

Figure 11:
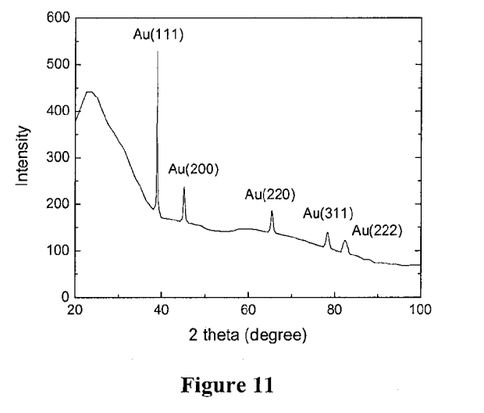
FIG. 11 shows measured X-ray diffraction patterns and major peaks of Au for island film formed by immersing a Si slide in Au sulfite solution for 30 min followed by annealing at 250° C. for 3 h.

FIG. 11 shows X-ray diffraction patterns and corresponding major peaks of crystalline phases of Au islands obtained by 30 minute-immersion of a Si slide in Au sulfite solution followed by 250° C. annealing (3 h). EL Au island films were predominantly Au(111) oriented. Noise appears along the diffraction patterns along with several small peaks corresponding to Au(200), (220), (311), and (222). The narrow (111) peak suggests crystallite size at the dominant orientation is very large. A broad peak <40° is believed to be due to a quartz substrate.

EXAMPLE 5

Preparation of Au Island Films by Drop-EL Plating Method

Figure 12:
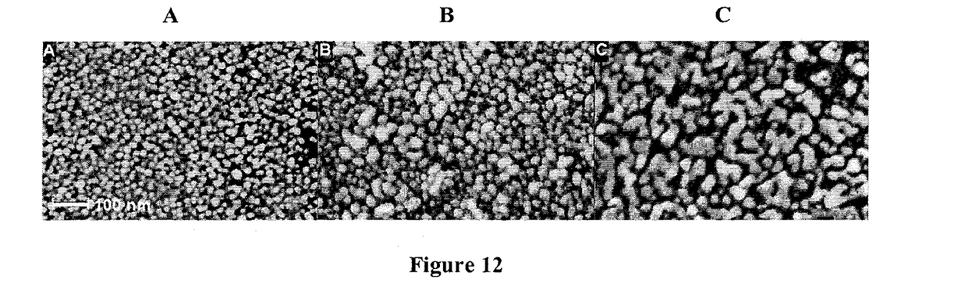
FIGS. 12A-C show SEM images after microliter-volume droplets of Au plating solution were deposited on fused quarts slides for exposure times of (A) 0.33 min, (B) 1 min and (C) 2 min, respectively, followed by annealing at 250° C. for 3 h.

Au was deposited on acid-etched tin-sensitized fused quartz slides via 1 to 5 μL droplets of Au plating solution. FIGS. 12A-C show SEM images of annealed (250° C., 3 h) slides after (A) 0.33, (B) 1, and (C) 2 min, respectively, of exposure to a droplet of EL plating solution. The plurality of Au nanoparticles in FIGS. 12A and 12B have diameters of (9.5±4.0) and (21.0±6.7) nm and densities of $2.59 \times 10^{11}$ and $9.15 \times 10^{10}$ particles per squared centimeter of analyzed substrate surface, respectively. FIG. 12A is similar to FIG. 1D, but with slightly smaller particles at a higher density. FIG. 12B appears intermediate between FIGS. 1D and 1E, containing some NP, with some remaining island structure. FIG. 12C appears comparable to FIG. 1E, with island structure predominating over nanoparticle structure. Comparing these images suggests that deposition rates from droplets and immersion are initially comparable (due to an abundance dissolved Au(I)). Deposition rate using droplets of plating solution is about half the deposition rate of complete immersion after about 2 minutes. Without wishing to be bound to any particular theory, the reduced deposition rate from droplets is believed attributed to the relative depletion of Au(I) from the finite 1-5 μL droplet reservoir, which in turn reduces the driving force for Au(I) diffusion to the surface. In contrast, immersion into a semi-infinite reservoir maintains a constant driving force after steady state is reached.

Au thin films from droplets, prior to annealing, exhibited red-PL peaks at wavelengths >600 nm and PL at ~500 nm similar to immersed samples. Annealing droplets produced similar trends in Au island films and NPs. However, extinction intensities of Au plated slides prepared by Au drops were ~24% smaller on average than the ones prepared by immersion in Au solution, reflecting the lower average deposition rate.

Spectral features of EL films are reflected in color changes under visual observation. EL plated quartz slides changed color after annealing at 250° C. (3 h) and changed color again after additional annealing at 800° C. (20 min). Au plated Si slides prepared by immersing Si slides in gold sulfite solution for 0.33, 1 and 4 minutes in Example 1 were almost transparent purple, bluish purple with little bit of gold color, and dense bluish purple with gold reflection, respectively. After annealing at 250° C. for 3 hours in Example 3, colors of slides changed to reddish purple with weak gold reflection, greenish blue with strong gold reflection, and thicker greenish blue with strong gold reflection, respectively. Annealing at 800° C. for 20 minutes in Example 4 changed these colors to red as Au island films transformed into NPs, with red intensity increasing in proportion to NP density. Au sputtered slides in Example 2 changed in color from greenish blue brown with weak gold reflection to greenish blue gold with strong gold reflection as sputtering time increases. Au drop plated Si slides prepared by drops of Au sulfite solution in Example 5 were initially almost colorless, slight brown, and bluish purple brown as Au plating time was increased from 0.33 to 0.67-1 and to 2 minutes, respectively. Au drop plated slides changed color after annealing at 250° C. to slight brown without gold reflection, pinkish purple with weak gold reflection, and blue with strong gold reflection, respectively. Annealing Au drop plated slides at 800° C. created red NPs.

EXAMPLE 6

Extinction Enhancement and SERS of Au NPs

The spectral features of the NPs are varied, for example, by controlling the interparticle separation distance, diameter and/or material composition of the NPs. These variable spectral features include: extinction efficiency, plasmon resonance, blue/red-shifts, and peakwidth. Tunable spectral features are used to enhance spectroscopic sensitivity. For example, surface enhanced Raman scattering (SERS) obtained using Au NP films on silica exhibit up to 16-fold enhancement of characteristic peaks that are maximized by tuning interparticle spacing of the NP films to excite plasmon resonance midway between laser excitation and Raman band (scattering) frequencies. Furthermore, the plasmon resonances of Au NPs are blue shifted as interparticle separation distance, D, decreases for D>80 nm=$\lambda/2\pi$=1/k where k is the wavevector and $\lambda$ is plasmon resonance. The plasmon peakwidths of Au NPs narrow for D>100 but broaden for smaller separations.

Spectral features are also varied by selecting different material compositions of the NPs, such as by using gold (Au) NPs rather than silver (Ag) NPs. As with Ag NPs, decreasing the interparticle distance of Au NPs first blue-shifts, then red-shifts the spectra; and introducing randomness in particle spacing red-shifts the plasmon resonance and increases its full-width at half-max. However, unlike for Ag NPs, the extinction efficiencies for Au NPs are enhanced as interparticle spacing decreases. Thus, a larger SERS is achieved by using Au NPs having a smaller interparticle spacing (i.e., greater surface density), and additional enhancement of extinction is achieved due to randomness in interparticle spacing of NPs.

Figure 13:
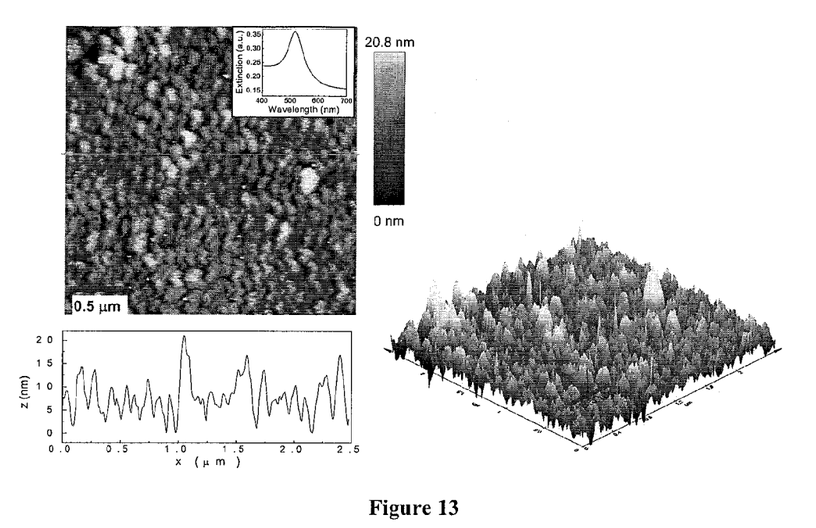
FIG. 13 shows AFM images in 2D and 3D of quartz slides exposed to microliter droplets of EL plating solution for 1 min, followed by annealing at 250° C. for 3 hr and heating at 800° C. for 20 min. The scanning area is 2.5 μm×2.5 μm. The depth scale is indicated by the vertical bar. A representative cross-section is shown under each 2D image. The solid line in the 2D image indicates the linear region where analysis was performed. Inset in 2D AFM image is the extinction UV-vis spectrum of the sample.

FIG. 13 shows 2D and 3D AFM images of Au NPs obtained using quartz slides exposed to microliter droplets of EL plating solution for 1 minute after annealing (250° C.; 3 h) and heating (800° C.; 20 min), resulting in a D/2r ratio of ~3.7. AFM tapping mode was employed. The scanning area was 2.5 µm×2.5 µm. A representative line scan is shown at the bottom of the 2D image, whose position is indicated by a solid line in the corresponding 2D image. For this sample NP dimension is about 96 nm, particle density is about 50 particles $\mu m^{-2}$ and average roughness (AR) is about 44 nm.

Figure 14:
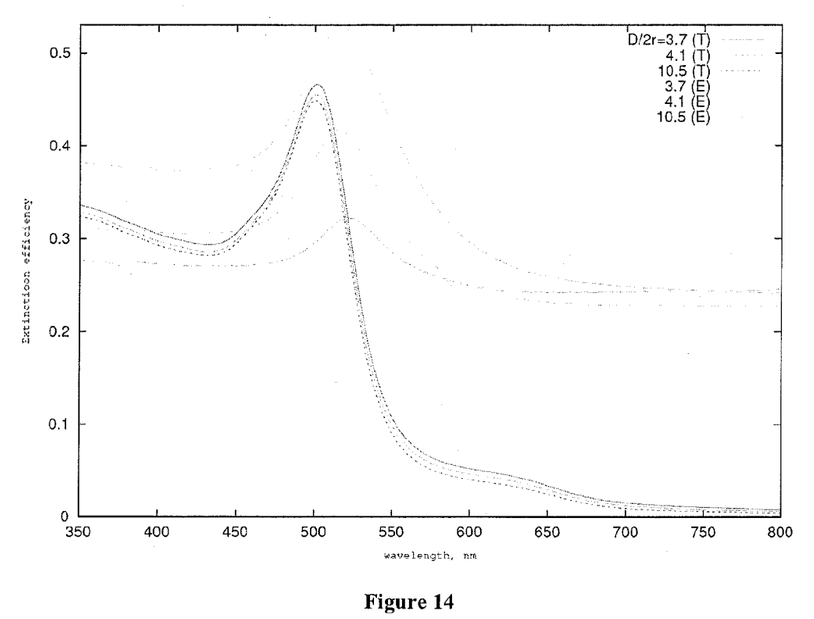
FIG. 14 is a plot of theoretical (T) and experimental (E) extinction efficiency versus wavelength for arrays of 20-nm gold nanoparticles (Au NPs) for different values of D/2r, where D is the interparticle separation distance and r is the nanoparticle radius. Experimental extinction spectra were converted to extinction efficiency using the relationship between absorbance and transmittance.

FIG. 14 compares theoretical extinction efficiencies for uniform square 2D arrays of 20-nm gold nanoparticles with experimental extinction efficiencies obtained spectrometrically from 2D arrays of 20-nm gold nanoparticles, such as those shown in FIG. 13. The semianalytical model shows peak extinction efficiency of Ag NPs decreases monotonically as D/2r approaches 1 for all r>5 nm. The same is true for Au NP with r>35 nm. However, Au NPs with r<35 nm exhibit enhanced extinction efficiency as D/2r approaches 1, increasing dramatically beginning at about D/2r~2-3. This theoretical enhancement is distinct from previous reports for Ag. This trend is illustrated by dotted lines in FIG. 14 for r=10 nm and D/2r=10.5 (blue), 4.1 (green) and 3.7 (red), respectively. The enhanced extinction efficiency that was predicted in the theoretical model is also observed in the experimental data. The close theoretical model agreement with the experimental data, coupled with the correct prediction of all experimental deviations, support the notion of sample optimization.

FIG. 14 also shows that randomness enhances extinction efficiency intensity in experimental spectra relative to theoretical spectra. Introducing randomness results in pairs of NP that are closer than those in square arrays. Without wishing to be bound to any particular theory, it is believed that these random pairs of closer particles dominate spectral changes, dramatically enhancing overall peak intensity as D/2r goes to 1. In addition, holes decrease peak extinction efficiency. Random removal of NP in the array, producing holes, dampens peak extinction efficiency and blue shifts the spectra for 20-nm Au NPs. The fewer particles in the field of view (FOV) (e.g., spacing of 214 nm relative to spacing of 66 nm) the larger the effect of removing a single NP, so this effect is greatest for large D/2r. The spacing of D/2r~3.7 has ten times as many particles in the FOV and D/2r~10, thus accounting for significant deviations between these spectra. Transmission is enhanced due to Plasmon re-emission as photon and photoluminescence decreases measured extinction relative to theoretical extinction. This applies for D<wavelength of light which is true for the experimental matrices. Extinction efficiency per NP in FOV is maximized for 214 nm spacing.

Figure 15:
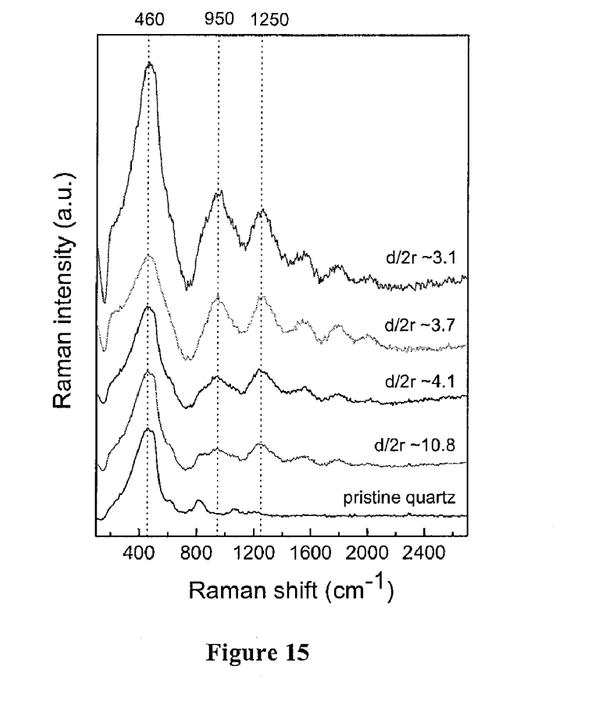
FIG. 15 shows plots of measured Raman spectra ($\lambda_{exc}$=488 nm, $P_{exc}$~15 mW) of the quartz slide and of the samples (produced using EL plating immersion and droplet methods) with different D/2r ratios. All the spectra are in the same y-scale. The spectra are offset for clarity. The vertical dotted lines represent the analyzed SERS bands frequencies (~460, 950 and 1250 $cm^{-1}$).

FIG. 15 shows Raman spectra ($\lambda_{exc}$=488 nm, $P_{exc}$~15 mW) of the pristine quartz slides (without gold NPs and any treatment) and of the samples produced using quartz slides exposed to EL plating immersion and droplet methods for different exposition times (from 0.33 up to 1 minute) and annealing and heating treatments, resulting in different D/2r ratios (from ~3.1 up to ~10.8). In general, the bands intensity increases as the D/2r ratio decreases. In order to quantify the apparent intensity increase in FIG. 15, the relative SERS enhancement factor (EF) is calculated with respect to quartz Raman bands intensity. The 460-, 950- and 1250-$cm^{-1}$ bands were analyzed.

Figure 16:
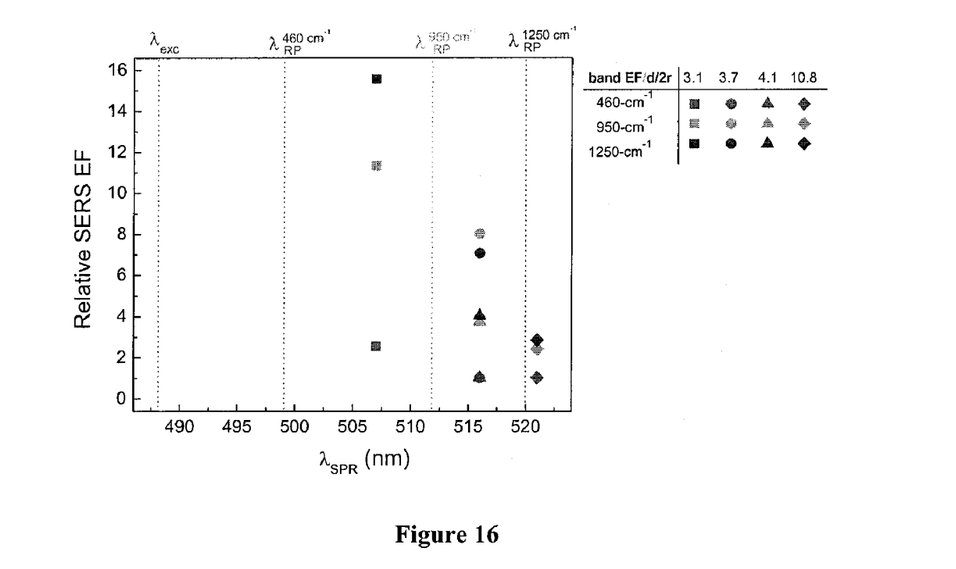
FIG. 16 shows plots of calculated relative surface enhanced Raman scattering (SERS) enhancement factor (calculated with respect to quartz Raman bands intensity) of the analyzed Raman bands (red points: 460 $cm^{-1}$; green points: 950 $cm^{-1}$; blue points: 1250 $cm^{-1}$) in FIG. 15 as a function of surface plasmon resonance peak wavelength of the samples with different D/2r ratios (squares: 3.1; circles: 3.7; triangles: 4.1; rhombuses: 10.8). The vertical dotted lines represent excitation ($\lambda_{exc}$=488 nm) and analyzed 460-, 950- and 1250-$cm^{-1}$ Raman bands wavelengths ($\lambda_{RP}$~499, 512 and 520 nm, respectively).

FIG. 16 shows relative SERS EF as a function of surface plasmon resonance peak wavelength ($\lambda_{SPR}$) of four samples with different D/2r ratios. Analyzed 460-, 950- and 1250-$cm^{-1}$ Raman band wavelengths ($\lambda_{RP}$~499, 512 and 520 nm, respectively) and $\lambda_{exc}$ are also showed using vertical dotted lines. The enhancement depends on the D12r ratio (EF increases as the D/2r ratio decreases) and on the relationship between excitation, surface plasmon resonance and analyzed Raman bands wavelengths ($\lambda_{SPR}$=($\lambda_{exc}$+$\lambda_{RP}$)/2). The obtained maximum EF occurs when $\lambda_{SPR}^{exp}$ is the closest to $\lambda_{SPR}^{theo}$ and agrees with the relationship $\lambda_{exc}$<$\lambda_{SPR}$<$\lambda_{RP}$, which corresponds to the sample with the smallest D/2r ratio. For a given $\lambda_{SPR}$ value, the EF is bigger when the D/2r ratio is smaller.

EXAMPLE 7

Optoelectronic Biosensor

A sensor is adapted to detect the presence of an analyte based on a spectroscopic signal change of the Au NPs disposed on the substrate surface. For example, a nanometer-sized gold (Au)-Silicon (Si) interface serves as antennae that are tunable both to a remote source of electromagnetism (EM), such as visible light, and to a nearby protein, nucleic acid, virus or other biological or chemical analytes. Light interacts with Au—Si antennae >$10^4$ times more efficiently than other matter, such as fluorophores. The light interaction induces concentrated electron vibrations (plasmons) that both spectroscopically sense nearby bio/chemical analytes and emit heat or other detectable EM frequencies. For example, detection may be based on a spectroscopic signal change in at least one of surface plasmon resonance or surface-enhanced Raman scattering. Monitoring for the spectroscopic signal change may be done automatically by an electronic computer interface that includes a photodetector and/or oscilliscope.

The sensor includes a capture ligand that is immobilized on the Au—Si surface and is capable of selectively binding to the analyte. For example, the capture ligand is capable of selective binding to the analyte, including a virus, DNA, or protein. Au nanoparticles may be functionalized with organic molecules, such as by using thiol-based chemistries, to immobilize the capture ligand onto the nanoparticle. Upon binding between the capture ligand and an analyte, polarized incident light is shifted, thus providing an optical signature to count and characterize the analyte. The sensor may include multiple pluralities of nanoparticles, wherein each plurality contains an average nanoparticle diameter and/or surface density that is different from at least one other plurality. Each plurality may be adapted to detect a change in spectroscopic signal at a different incident or reflected wavelength than at least one other plurality. Each plurality may be tuned to a different portion of the signal spectrum. Each plurality can be functionalized with a different capture ligand in order to detect the presence of a different analyte in solution.

The sensor may include a Au—Si plasmon capillary structure that increase coupling of light and plasmons >100-fold to produce corresponding increases in detection sensitivity and EM generation. Plasmon capillaries can be miniaturized to <100-nm dimensions and ≦10-nanosecond response times, reducing sample volumes and turnaround times dramatically. The capillary may comprise a 3-D surface or internal surface, such as the surface within a tube or microfluidic container. The capillary surface may be adapted for optically-induced biosensing and thermal analysis. The capillary surface described by D. K. Roper, Chem. Eng. Sci. (2007) 62:1288-1996, which is incorporated herein by reference in its entirety, may be used.

The sensor may include an 'analyte-pull' sampling structure to improve detection sensitivity and/or response time by 10-fold, especially in large-volume, complex matrices. For example, the analyte-pull structure can be that described by D. K. Roper, Chem. Eng. Sci. (2006) 61(8) 2557-2564, which is incorporated herein by reference in its entirety.

The sensor may also facilitate investigating photon interactions with metal-dielectric interface-bound plasmon polaritons in EL island films or nanoparticles. The sensor is adapted to be a nanoscopic, efficient opto-electronic device (e.g., electro-optic modulator) and/or substrate for near-field microscopy. Improved stability offers the possibility of using Au island films or nanoparticles to provide a near-field transmission signal to identify position of nano-clusters and crevices on the metal surface via near-field scanning optical microscopy (NSOM).

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

What is claimed is:

1. A method of making nanoparticles comprising a first noble metal, the method comprising:
    performing electroless plating in to form an island film on a tin-sensitized surface by:
        depositing a droplet of a solution comprising a nanoparticle precursor onto a second noble metal disposed on the surface, wherein the droplet comprises a volume less than about 20 microliter, and wherein the nanoparticle precursor comprises ions of the first noble metal; and
        galvanically displacing the second noble metal with the nanoparticle precursor, wherein the second noble metal is less noble than the first noble metal; and
    annealing the island film to form the nanoparticles, wherein an average diameter of the nanoparticles is controlled during processing from about 5 nm to about 300 nm by controlling the island film thickness or annealing conditions.

2. The method of claim 1, wherein:
    the solution comprises dissolved $Na_3Au(SO_3)_2$;
    the tin-sensitized surface comprises a surface formed by exposing a silicon dioxide surface to tin ions;
    the second noble metal comprises silver; and
    the first noble metal comprises gold.

* * * * *

UNITED STATES PATENT AND TRADEMARK OFFICE
CERTIFICATE OF CORRECTION

PATENT NO. : 8,097,295 B2
APPLICATION NO. : 12/038088
DATED : January 17, 2012
INVENTOR(S) : Donald Keith Roper et al.

Page 1 of 1

It is certified that error appears in the above-identified patent and that said Letters Patent is hereby corrected as shown below:

IN THE CLAIMS

Column 20, Line 13, in Claim 1, delete "plating in to" and insert -- plating to --.

Signed and Sealed this
First Day of October, 2013

Teresa Stanek Rea
*Deputy Director of the United States Patent and Trademark Office*